United States Patent [19]

Schurter et al.

[11] Patent Number: 4,935,051

[45] Date of Patent: Jun. 19, 1990

[54] 2-[4-(5-CHLORO-3-FLUOROPYRIDIN-2-YLOXY)-PHENOXYL]-PROPIONIC ACID METHYL ESTER WITH HERBICIDAL ACTIVITY

[75] Inventors: Rolf Schurter, Binningen; Hermann Rempfler, Ettingen, both of Switzerland

[73] Assignee: Ciba-Geigy Corporation, Ardsley, N.Y.

[21] Appl. No.: 858,798

[22] Filed: May 2, 1986

Related U.S. Application Data

[63] Continuation-in-part of Ser. No. 677,775, Dec. 3, 1984, abandoned, which is a continuation-in-part of Ser. No. 450,815, Dec. 20, 1982, Pat. No. 4,505,743.

[30] Foreign Application Priority Data

Dec. 31, 1981 [CH] Switzerland ............ 8372/81

[51] Int. Cl.$^5$ ............ C07D 213/64; A01N 43/40
[52] U.S. Cl. ............ 71/94; 546/302
[58] Field of Search ............ 546/302; 71/94

[56] References Cited

U.S. PATENT DOCUMENTS 4,505,743  3/1985  Schurter et al. ............ 71/94
4,565,568  1/1986  Johnston et al. ............ 71/94

*Primary Examiner*—Alan L. Rotman
*Attorney, Agent, or Firm*—Bruce M. Collins; Edward McC. Roberts

[57] ABSTRACT

There is described the novel 2-[4-(5-Chloro-3-fluoropyridin-2-yloxy)-phenoxy]-propionic acid methyl ester and its (R)-enantiomer.

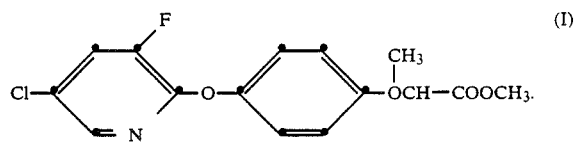

These compounds are suitable for selectively controlling weeds in crops of cultivated plants, and for reducing the growth of grasses.

10 Claims, No Drawings

2-[4-(5-CHLORO-3-FLUOROPYRIDIN-2-YLOXY)-PHENOXYL]-PROPIONIC ACID METHYL ESTER WITH HERBICIDAL ACTIVITY

CROSS-REFERENCE TO RELATED APPLICATION

This is a continuation-in-part of our application Ser. No. 677.775, filed Dec. 3, 1984, abandoned which in turn is a continuation-in-part of our application Ser. No. 450,815, filed Dec. 20, 1982, now U.S. Pat. No. 4,505,743, issued Mar. 19, 1985.

The present invention relates to the novel 2-[4-(5-Chloro-3-fluoropyridin-2-yloxy)-phenoxy]-propionic acid methyl ester, its (R)-enantiomer, to their production, to compositions containing these esters as active ingredients, and also to the use thereof as herbicides in general, and in particular for controlling weeds in crops of cultivated plants, such as cereals, rice, maize, soyabean and sugar beet. The 2-[4-(5-Chloro-3-fluoropyridin-2-yloxy)-phenoxy]propionic acid-methyl ester corresponds to the formula I

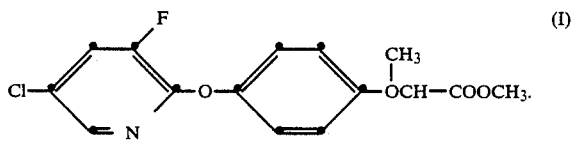

This invention comprises also the enantiomer (R)-2-[4-(5-chloro-3-fluoropyridin-2-yloxy)-phenoxy]-propionic acid methyl ester.

The 2-[4-(5-Chloro-3-fluoropyridin-2-yloxy)-phenoxylpropionic acid methyl ester and its enantiomer are characterised by a good action against mono- and some dicotyledonous weeds; they are above all effective in the post-emergence process against undesirable weeds and wild grasses occurring in cultivated crops, such as crops of cereals, maize, rice, soyabean and sugar beet. A particularly valuable aspect is that it is possible with the novel derivatives to combat wild grasses which are very difficult to control, for example Avena fatua, Avena sterilis, Alopecurus myosuroides, Lolium perenne, Phalaris sp. Bromus tectorum and various species of Setaria and Panicum. The action under field conditions is achieved even with small applied amounts of less than 1 kg per hectare, at which levels the cultivated crops are not harmed, or are harmed to only a negligible extent.

Halopyridyloxy-α-phenoxy-propionic acid derivatives have been described in numerous publications (cp. for example the German Offenlegungsschriften Nos. 2,546,251, 2,649,706, 2,714,622 and 2,715,284, and the European Publications Nos. 483 and 1473). The amounts applied can vary within wide limits, for example between 0.05 and 5 kg of active substance per hectar.

The novel ester of the formula I can be produced by reacting 5-chloro-2,3-difluoropyridine of the formula II

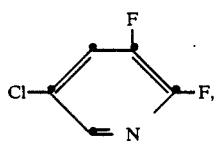

in an inert solvent or diluent and in the presence of the equimolar amount of a base, with the racemic or enantiomeric 4-hydroxyphenoxy-α-propionic acid methyl ester of the formula III

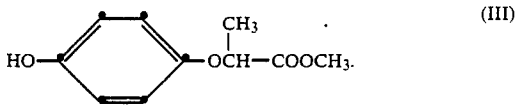

A second process comprises reacting a 4-(5-chloro-3-fluoropyridin-2-yloxy)-phenol of the formula IV

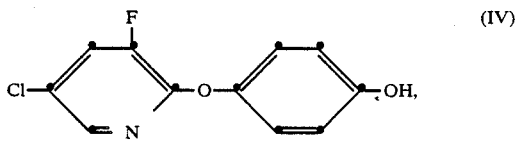

in an inert solvent or diluent and in the presence of the equimolar amount of a base, with the racemic or enantiomeric α-halopropionic acid methyl ester of the formula V

wherein Hal'is halogen.

A further process comprises reacting the racemic or enantiomeric 2-[4-(5-chloro-3-fluoropyridin-2-yloxy)-phenoxy]-propionic acid halide of the formula VI

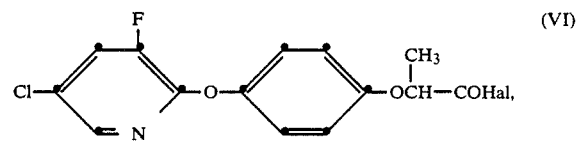

wherein Hal is halogen, in an inert solvent or diluent and in the presence of the equimolar amount of a base, with methanol.

In addition, the ester of the formula I can be produced by reacting the racemic or enantiomeric 2-[4-(5-chloro-3-fluoropyridin-2-yloxy)-phenoxy]-propionic acid of the formula IX

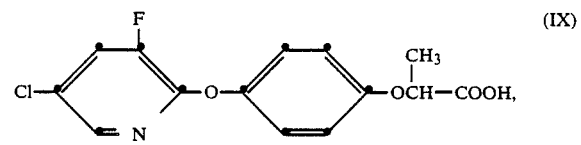

in an inert solvent or diluent and in the presence of the equimolar amount of a base, with a methyl halide of the formula X

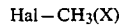

wherein Hal is halogen.

Finally, a further process comprises converting the racemic or enantiomeric 2-[4-(3-amino-5-chloropyridin-2-yloxy)phenoxy]-propionic acid-methyl ester of the formula XI

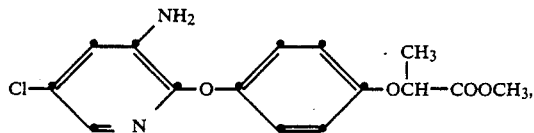

(XI)

using known methods, into a diazonium salt, and converting this further into the fluorine compounds.

The (R)-enantiomer of the ester of formula I is also prepared by reacting in an inert organic solvent in the presence of a base 4-(5-chloro-3-fluoropyridin-2-yloxy)-phenol of the formula IV

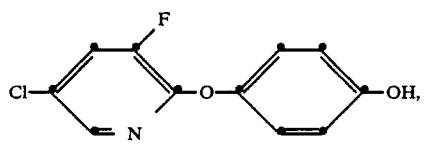

(IV)

with (S)-lactic acid methylester-sulfonate of the formula XII

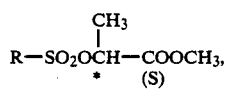

(XII)

(S)

wherein R is a $C_1$–$C_6$ alkyl group which is straight-chain or branched, and which is unsubstituted or substituted by halogen, cyano, $C_1$–$C_4$ alkoxycarbonyl or is a phenyl group which is unsubstituted or substituted by $C_1$–$C_4$ alkyl, $C_1$–$C_4$ alkoxy, halogen, nitro, cyano, $C_1$–$C_4$ alkoxycarbonyl and isolating the resulting (R)(+)-2[4-(5-chloro-3-fluoro-pyridin-2-yloxy)-phenoxy]-propionic acid-methyl ester obtained from the reaction-mixture.

The starting material of formula II 5-chloro-2,3-difluoropyridine may be prepared by fluorinating the corresponding 2,3,5-trichloropyridine in the presence of cesium fluoride. The products can be distilled off the reaction mixture and have to be purified by fractionate distillation. It is also possible to obtain 5-chloro-2,3difluoropyridine starting from 2,5-dichloro-3-nitropyridine, which is reduced by means of hydrogen in the presence of e.g. Raney-nickel catalyst to 3-amino-2,5-dichloropyridine. This compound is then converted with sodium nitrite in the presence of hydrofluoric acid to 2,5-dichloro-3-fluoropyridine. This latter product can then be fluorinated in a good yield by means of potassium-fluoride to 2,3-difluoro-5-chloropyridine.

The starting material of formula IV, 4-(5-chloro3-fluoropyridin-2-yloxy)-phenol can be obtained by condensing, in an inert organic solvent and in the presence of a base 5-chloro-2,3-difluoropyridine and hydroquinone.

The starting material of formula XI can be obtained e.g. by reducing in the presence of hydrogen the corresponding racemic or enantiomeric 2-[4-(5-chloro-3-nitropyridin-2-yloxy)-phenoxy]-propionic acid methyl ester known e.g. from the German Offenlegungsschrift DE-A 2 732 846.

The remaining starting material are either known or can easily be prepared by conventional means.

A number of these reactions are advantageously carried out in an organic solvent or diluent inert to the reactants, for example an alcohol, ester, ether, ketone, dimethylformamide, dimethyl sulfoxide, acetonitrile, 1,1-dioxy-tetrahydrothiophene or an aromatic compound, such as toluene and xylene.

The reaction temperatures are between $-10°$ C. and $150°$ C., in practice however between room temperature and the boiling point of the solvent Depending on the chosen starting material, the solvent and the temperature, the reaction time is between 1 hour up to about 1 day Where a halogen atom is detached in the reaction, the equimolar amount of an acid-binding agent should be used Suitable as such is essentially any inorganic or organic base, for example NaOH, KOH, NaHCO$_3$, K$_2$CO$_3$ or K-tertbutylate, and amines, such as trimethylamine, triethylamine, pyridine, 4-dimethylaminopyridine, and so forth.

The novel active substances of the formula I are stable compounds which are soluble in customary organic solvents, such as alcohols, ethers, ketones, dimethylformamide, dimethyl sulfoxide, and the like. The compounds show favorable results in chronical toxicity studies to mammals.

The compounds of the formula I are used either in an unmodified form or preferably together with auxiliaries customarily employed in formulation practice, and are thus processed in a known manner for example into the form of emulsion concentrates, directly sprayable or dilutable solutions, diluted emulsions, wettable powders, soluble powders, dusts or granulates, and also encapsulations in for example polymeric substances. The application processes, such as spraying, atomising, dusting, scattering or pouring, and likewise the type of composition, are selected to suit the objectives to be achieved and the given conditions.

The formulations, that is to say, the compositions or preparations containing the active substance of the formula I and optionally a solid or liquid additive, are produced in a known manner, for example by the intimate mixing and/or grinding of the active substances with extenders, such as with solvents, solid carriers and optionally surface-active compounds (tensides).

Suitable solvents are: aromatic hydrocarbons, preferably the fractions $C_8$ to $C_{12}$, such as xylene mixtures or substituted naphthalenes, phthalic esters, such as dibutylor dioctylphthalate, aliphatic hydrocarbons, such as cyclohexane or paraffins, alcohols and glycols, as well as ethers and esters thereof, such as ethanol, ethylene glycol, ethylene glycol monomethyl or -ethyl ethers, ketones such as cyclohexanone, strongly polar solvents, such as N-methyl-2-pyrrolidone, dimethyl sulfoxide or dimethylformamide, as well as optionally epoxidised vegetable oils, such as epoxidised coconut oil or soybean oil; or water.

The solid carriers used, for example for dusts and dispersible powders, are as a rule natural mineral fillers, such as calcite, talcum, kaolin, montmorillonite or attapulgite. In order to improve the physical properties, it is possible to add highly dispersed silicic acid or highly dispersed absorbent polymers. Suitable granulated adsorptive carriers are porous types, for example pumice, ground brick, sepiolite or bentonite; and suitable nonsorbent carriers are materials such as calcite or sand. There can also be used a great number of pre-granulated materials of inorganic or organic nature, such as in particular dolomite or ground plant residues.

Suitable surface-active compounds are, depending on the nature of the active substance of the formula I to be formulated, nonionic, cationic and/or anionic tensides having good emulsifying, dispersing and wetting properties By 'tensides' are also meant mixtures of tensides.

Suitable anionic tensides are both so-called water-soluble soaps as well as water-soluble, synthetic, surface-active compounds.

Soaps which are applicable are for example the alkali metal, alkaline-earth metal or optionally substituted ammonium salts of higher fatty acids ($C_{10}$-$C_{20}$), for example the Na or K salts of oleic or stearic acid, or of natural fatty acid mixtures, which can be obtained for example from coconut oil or tallow oil. Also to be mentioned are the fatty acid-methyl-taurine salts.

So-called synthetic tensides are however more frequently used, particularly fatty sulfonates, fatty sulfates, sulfonated benzimidazole derivatives or alkylarylsulfonates. The fatty sulfonates or sulfates are as a rule in the form of alkali metal, alkaline-earth metal or optionally substituted ammonium salts, and contain an alkyl group having 8 to 22 C atoms, 'alkyl' including also the alkyl moiety of acyl groups, for example the Na or Ca salt of ligninsulfonic acid, of dodecylsulfuric acid ester or of a fatty alcohol sulfate mixture produced from natural fatty acids. Included among these are also the salts of sulfuric acid esters and sulfonic acids of fatty alcohol ethylene oxide adducts. The sulfonated benzimidazole derivatives preferably contain 2 sulfonic acid groups and a fatty acid group having 8–22 C. atoms. Alkyarylsulfonates are for example the Na, Ca or triethanolamine salts of dodecylbenzenesulfonic acid, of dibutylnaphthalenesulfonic acid or of a naphthalenesulfonic acid-formaldehyde condensation product. Also suitable are corresponding phosphates, for example salts of the phosphoric ester of a p-nonylphenol-(4–14)ethylene oxide adduct.

Suitable nonionic tensides are in particular polyglycol ether derivatives of aliphatic or cycloaliphatic alcohols, saturated or unsaturated fatty acids and alkylphenols, which can contain 3 to 30 glycol ether groups and 8 to 20 carbon atoms in the (aliphatic) hydrocarbon radical and 6 to 18 carbon atoms in the alkyl moiety of the alkylphenols.

Further suitable nonionic tensides are the water-soluble polyethylene oxide adducts, which contain 20 to 250 ethylene glycol ether groups and 10 to 100 propylene glycol ether groups, with polypropylene glycol, ethylenediaminopolypropylene glycol and alkylpolypropylene glycol having 1 to 10 carbon atoms in the alkyl chain. The compounds mentioned usually contain 1 to 5 ethylene glycol units per propylene glycol unit. Examples of nonionic tensides which may be mentioned are: nonylphenolpolyethoxyethanols, castor oil polyglycol ethers, polypropylene/polyethyleneoxy adducts, tributylphenoxypolyethoxyethanol, polyethylene glycol and octylphenoxypolyethoxyethanol. Suitable also are fatty acid esters of polyoxyethylenesorbitan, such as polyoxyethylenesorbitan-trioleate.

In the case of the cationic tensides, they are in particular quaternary ammonium salts which contain as N-substituents at least one alkyl group having 8 to 22 carbon atoms and, as further substituents, lower, optionally halogenated alkyl, benzyl or lower hydroxyalkyl groups. The salts are preferably in the form of halides, methyl sulfates or ethyl sulphates, for example stearyltrimethylammonium chloride or benzyldi(2-chloroethyl)ethylammonium bromide.

The tensides customarily used in formulation practice are described, inter alia, in the following publications:

"Mc Cutcheon's Detergents and Emulsifiers Annual", MC Publishing Corp., Ridgewood, New Jersey, 1979, Sisely and Wood, "Encylopedia of Surface Active Agents", Chemical Publishing Co., Inc. New York, 1964.

These preparations contain as a rule 0.1 to 99%, particularly 0.1 to 95%, of active substance of the formula I, 1 to 99% of a solid or liquid additive, and 0 to 25%, especially 0.1 to 25%, of a tenside.

Whereas commercial products are preferably in the form of concentrated compositions, the compositions employed by the end-user are as a rule diluted.

The compositions can also contain further additives, such as stabilisers, antifoaming agents, viscosity regulators, binders and adhesives, and also fertilisers or other active ingredients for obtaining special effects.

The following Examples describe in detail the production of 2-[4-(3-fluoro-5-chloropyridin-2-yloxy)-phenoxy]-propionic acid methyl esters and also compositions containing such esters as active ingredients. Percentages relate to weight.

EXAMPLE 1

Preparation of 2-[4-(5-chloro-3-fluoropyridin-2-yloxy)phenoxy]propionic acid methyl ester

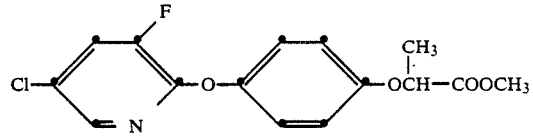

8.2 g (0.025 mol) of 2-[4-3-amino-5-chloropyridin-2yloxy)-phenoxy]-propionic acid methyl ester are dissolved in 120 ml of hydrofluoroboric acid d($HBF_4$, 50%), and the solution is cooled to 0° C. There are then added dropwise 1.87 g (0.027 mol) of sodium nitrite in 20 ml of water during one hour. The product is filtered off after a further hour; it is then washed and (at room temperature and over phosphorus pentoxide) well dried. The diazonium-tetrafluoroborate thus obtained is heated at 150° C. for 10 minutes. The residue is dissolved still hot in methanol and, after the addition of an amount of active charcoal, it is filtered, and concentrated in a rotary evaporator. The yield after purification through a silica gel column (eluted with methylene chloride/hexane 6:1) is 5.5 g (67% of theory) of the title compound; m.p. 63–64° C.

EXAMPLE 2

Preparation of 2-[5-chloro-3-fluoropyridin-2-yloxy)-phenoxy]propionic acid methyl ester

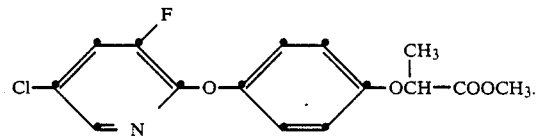

To a stirred mixture of 21.6 g (0.11 mol) of 2-(4-hydroxyphenoxy)-propionic acid methyl ester, 15.2 g (0.11 mol) of potassium carbonate, 1.45 g (0.0055 mol) of 18-Crown-6 ether and 100 ml of acetonitrile is added dropwise a solution of 14.95 g (0.10 mol) of 5-chloro-2,3-difluoropyridine in 30 ml of acetonitrile and the mixture is heated at a temperature of 50 to 60° C. during 40 hours. The mixture is then poured into ice/water. The organic material is extracted with ethyl acetate, washed with a saturated salt solution, dried over magnesium sulfate, filtered and evaporated. The oily residue is purified by chromatography over a silicagel column with a hexane/ethyl acetate 3:1 solvent. After evaporation of the solvent 20.4 g of the above ester (63 % of the theory) is obtained in crystalline form. The melting point is 63–64° C.

The 5-chloro-2,3-difluoropyridine necessary as starting material is obtained as follows (a) 3-amino-2,3-dichloropyridine To a solution of 129.2 g (0.69 mol) of 2,5-dichloro-3-nitropyridine in 1300 ml of dioxane is added 26 0 g of Raney-nickel, that has previously been washed with ethanol. This mixture is then hydrogenated with hydrogen under normal pressure at 20–35° C. After uptake of 20% of the theoretical amount of hydrogen, another 30 g of washed Raney-nickel catalyst are added. After hydrogenating for 22 hours, the catalyst is filtered off, the solvent is evaporated and the residue is crystallized from hexane/ ethyl acetate. Thus, 84.9 g of 3-amino-2,5-dichloropyridine (78% of the theory) are obtained, which melts at 129–132° C.

(b) 2,5-dichloro-3-fluoropyridine

To 450 ml (22.5 mol) of hydrogen fluoride in a stainless steel reaction vessel are added at a temperature of −5 to −1°, 163 g (1.0 mol) of 3-amino-2,5-dichloropyridine. Then there are added while stirring at the same temperature 82.8 g (1.2 mol) of sodium nitrite into the solution The reaction mixture is stirred for 1.5 hours at −5 to −1°, then the temperature is slowly raised to +60° C. After the evolution of gas has ceased, the hydrogen fluoride is distilled off and the residue is taken up in methylen chloride. Ice/water is then added thereto and the cold mixture is neutralized with concentrated ammonium hydroxide solution. The organic phase separated and the water phase is extracted three times with methylene chloride. The organic phases are washed with water, dried over magnesium sulfate, filtered through silicagel and evaporated. Thus, 141.5 g (85% of the theory) of 2,5-dichloro-3-fluoropyridine are obtained.

(c) 5-chloro-2,3-difluoropyridine

A suspension of 64.6 g (1.1 mol) of potassium fluoride and 11.25 g (0.075 mol) of cesium-fluoride in 240 ml of sulfolane (1,1-dioxo-tetrahydrothiophene) is heated to 140° C. By reducing the pressure 50 ml of sulfolane are distilled off. To the suspension a solution of 61.4 g (0.37 mol) of 2,5-dichloro-3-fluoropyridine in 20 ml of sulfolane is added.

The reaction-mixture is then stirred for 35 hours at a temperature of 140°, cooled and poured into ice/water. The organic material is extracted with ether. The ethereal layer is washed with water dried over magnesium sulfate, filtered and evaporated to yield 48.7 g of a colourless oil (88% of the theory) which boils at 65–66° at 133 mbar.

EXAMPLE 3

Preparation of the (R)(+)-2-[4-(5-chloro-3-fluoropyridin-2-yloxy)-phenoxy]-propionic acid methyl est

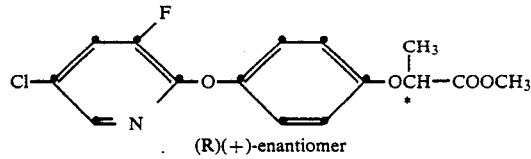

(R)(+)-enantiomer

A solution of 24 g (0.1 mol) of 4-(5-chloro-3-fluoropyridin-2-yloxy)-phenol in 80 ml of dimethylsulfoxide is added dropwise to a stirred solution of 13.8 g (0.1 mol) of potassium carbonate in 50 ml of dimethylsulfoxide. When everything is added, the mixture is stirred for 2 hours at room temperature and then a solution of 25.8 g (0.1 mol) of(S)(−)-lactic acid-methylester tosylate is added dropwise over 30 minutes. The mixture is heated to 60° and stirred at that temperature for 20 hours, then poured onto ice/water and the organic material is extracted three times with ether. The ether-layer is washed with water and saturated salt solution, dried over magnesium sulfate, filtered and evaporated. The residue is passed for purification through a silicagel column with a hexane/ethyl acetate 3:1 solvent. After distillation of the solvent, 26 g of a clear oil of the above ester is obtained ($[\alpha]^{20}/_D = +38.8 \pm 0.5°$ 2% in acetone).

The 4-(5-chloro-3-fluoropyridin-2-yloxy)-phenol is obtained as follows:

(a) A mixture of 27.5 g (0.25 mol) of hydroquinone, 11.2 g (0.2 mol) of potassium hydroxide in 600 ml of dimethylsulfoxide is stirred at room temperature under a nitrogen atmosphere until everything is dissolved. A solution of 30 g (0.2 mol) of 5-chloro-2,3difluoropyridine in 200 ml of dimethylsulfoxide is added dropwise thereto. The reaction mixture is then heated to 70° and stirred at that temperature for 4 hours. Then it is poured into ice/water and the mixture is acidified with hydrochloric acid, extracted with ethyl acetate, dried over magnesium sulfate, filtered and evaporated to dryness. The residue is taken up in a hexane/ethyl acetate 2 1 solvent and passed over a silicagel column for purification. After concentrating the eluate, the residue crystallizes to yield 33 g of white crystals, melting at 97–98°.

EXAMPLE 4

Preparation of (R)(+)-2-[4-(5-chloro-3-fluoropyridin-2-yloxy)phenoxy]-propionic acid-methyl ester

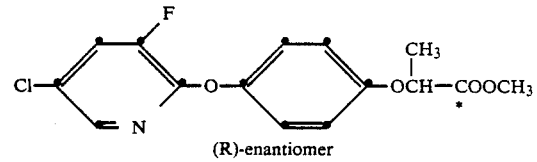

(R)-enantiomer

A solution of 10.6 g (0.030 mol) of (R)(+)-2-[4-(5-chloro-3-fluoropyridin-2-yloxy)-phenoxy]-propionic acid chloride in 100 ml toluene is added slowly, while stirring into a solution of 4.9 ml (0.035 mol) of triethylamine and 2 ml (0.035mol) of methanol in 40 ml of toluene, that is cooled in an ice/bath. When everything is added, the ice-bath is removed and the reaction mixture is stirred for 3 hours at room temperature. The reaction mixture is then poured into ice-water and the organic material is extracted twice with ethyl acetate. The ethyl acetate layer is washed with a saturated salt solution, dried over magnesium sulfate, filtered and evaporated. The residue is purified by chromatography over a silicagel column with a hexane/ethyl acetate solution. After evaporation of the solvent, a clear oil, the above ester remains $n^{35}_D$ 1.5859, $[\alpha]^{20}_D = +38.8 \pm 0.5$ (2 % acetone).

EXAMPLE 5

Production of a formulation with liquid active ingredients of the formula 1 (%=per cent by weight)

| Emulsion concentrates | (a) | (b) | (c) |
|---|---|---|---|
| 2-[4-(5-chloro-3-fluoropyridin-2-yloxy)-phenoxy]-propionic acid methyl ester | 20% | 40% | 50% |
| calcium dodecylbenzenesulfonate | 5% | 8% | 5.8% |
| castor oil-polyethylene glycol ether (36 mols of ethylene oxide) | 5% | — | — |
| tributylphenol-polyethylene glycol ether (30 mols of ethylene oxide) | — | 12% | 4.2% |
| cyclohexanone | — | 15% | 20% |
| xylene mixture | 70% | 25% | 20% |

Emulsions of any required concentration can be produced from concentrates of this type by dilution with water.

| Solutions | (a) | (b) | (c) | (d) |
|---|---|---|---|---|
| 2-[4-(3-chloro-5-fluoropyridin-2-yloxy)-phenoxy]-propionic acid methyl ester | 80% | 10% | 5% | 95% |
| ethylene glycol-monomethyl ether | 20% | — | — | — |
| polyethylene glycol MG 400 | — | 70% | — | — |
| N-methyl-2-pyrrolidone | — | 20% | — | — |
| epoxidised coconut oil | — | — | 1% | 5% |
| ligroin (boiling limits 160–190° C.) | — | — | 94% | — |

The solutions are suitable for application in the form of very fine drops.

| Granulates | (a) | (b) |
|---|---|---|
| (R)(+)2-[4-(5-chloro-3-fluoropyridin-2-yloxy)-phenoxy]-propionic acid methyl ester | 5% | 10% |
| kaolin | 94% | — |
| highly dispersed silicic acid | 1% | — |
| attapulgite | — | 90% |

The active ingredient is dissolved in methylene chloride; the solution is subsequently sprayed onto the carrier, and the solvent is evaporated off in vacuo.

| Dusts | (a) | (b) |
|---|---|---|
| 2-[4-(5-chloro-3-fluoropyridin-2-yloxy)-phenoxy]-propionic acid methyl ester | 2% | 5% |
| highly dispersed silicic acid | 1% | 5% |
| talcum | 97% | — |
| kaolin | — | 90% |

Ready-for-use dusts are obtained by the intimate mixing together of the carriers with the active ingredient.

Formulation Examples for solid active ingredients of the formula I (%=per cent by weight)

| Wettable powders | (a) | (b) |
|---|---|---|
| 2-[4-(5-chloro-3-fluoropyridin-2-yloxy)-phenoxy]-propionic acid methyl ester | 20% | 60% |
| sodium lignin sulfonate | 5% | 5% |
| sodium lauryl sulfate | 3% | — |
| sodium diisobutylnaphthalene sulfonate | — | 6% |
| octylphenolpolyethylene glycol ether (7–8 mols of ethylene oxide) | — | 2% |
| highly dispersed silicic acid | 5% | 27% |
| kaolin | 67% | — |

The active ingredient is well mixed with the additives and the mixture is thoroughly ground in a suitable mill. Wettable powders which can be diluted with water to give suspensions of the required concentration are obtained.

| Emulsion concentrate | |
|---|---|
| (R)(+)2-[4-(5-chloro-3-fluoropyridin-2-yloxy)-phenoxy]-propionic acid methyl ester | 10% |
| octylphenol polyethylene glycol ether (4–5 mols of ethylene oxide) | 3% |
| calcium dodecylbenzenesulfonate | 3% |
| castor oil polyglycol ether (36 mols of ethylene oxide) | 4% |
| cyclohexanone | 30% |
| xylene mixture | 50% |

Emulsions of the required concentration can be obtained from this concentrate by dilution with water.

| Dusts | (a) | (b) |
|---|---|---|
| 2-[4-(5-chloro-3-fluoropyridin-2-yloxy)-phenoxy]-propionic acid methyl ester | 5% | 8% |
| talcum | 95% | — |
| kaolin | — | 92% |

Dusts ready for use are obtained by mixing the active substance with the carriers and grinding the mixture in a suitable mill.

| Extruder granulate | |
|---|---|
| 2-[4-(5-chloro-3-fluoropyridin-2-yloxy)-phenoxy]-propionic acid methyl ester | 10% |
| sodium lignin sulfonate | 2% |
| carboxymethylcellulose | 1% |
| kaolin | 87% |

The active ingredient is mixed and ground with the additives, and the mixture is moistened with water. This mixture is extruded and then dried in a stream of air.

| Coated granulate | |
|---|---|
| 2-[4-(5-chloro-3-fluoropyridin-2-yloxy)-phenoxy]-propionic acid methyl ester | 3% |
| polyethylene glycol (MG 200) | 3% |
| kaolin | 94% |

The finely ground active ingredient is evenly applied, in a mixer, to the kaolin moistened with polyethylene glycol. Dustfree coated granulates are obtained in this manner.

| Suspension concentrate | |
|---|---|
| (R)-2-[4-(5-chloro-3-fluoropyridin-2-yloxy)-phenoxy]-propionic acid methyl ester | 40% |
| ethylene glycol | 10% |
| nonylphenolpolyethylene glycol ether (15 mols of ethylene oxide) | 6% |
| sodium lignin sulfonate | 10% |
| carboxymethylcellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is thus obtained a suspension concentrate from which can be produced, by dilution with water, suspensions of the concentration required.

EXAMPLE 6: Herbicidal action

Pre-emergence herbicidal action (inhibition of germination)

Immediately after sowing of the test plants in pots in a greenhouse, the surface of the soil is sprayed with an aqueous dispersion of the active ingredient, which has been prepared either from a 25% emulsion concentrate, or from a 25% wettable powder in the case of active ingredients which cannot be prepared as emulsion concentrates owing to inadequate solubility. Varying concentrations are used, and the amount of active ingredient is calculated on the basis of kg per hectare. The pots are then kept in a greenhouse at 22–25° C. with 50–70% relative humidity, and are regularly watered. The test results are evaluated after three weeks.

The condition of the plants is assessed according to the following scale of ratings:

| 9 | plant has flourished as in the case of the untreated control plant, |
|---|---|
| 6–8 | slight damage, plant can recover, |
| 4–5 | medium damage, stunted growth, |
| 2–3 | severe damage, |
| 1 | plant has died or has not germinated. |

| | Compound | |
|---|---|---|
| Applied amount | 1 | A |
| kg/hectare | 1 ½ ¼ | 1 ½ ¼ |
| plant | | |
| wheat | 2 6 7 | 8 9 9 |
| soyabean | 9 9 9 | 7 9 9 |
| cotton | 9 9 9 | 9 9 9 |
| sugar beet | 9 9 9 | 9 9 9 |
| Avena fatua | 1 2 2 | 6 9 9 |
| Bromus tectorum | 1 1 1 | 4 8 9 |
| Alopecurus myos. | 1 1 1 | 3 9 9 |
| Digitaria sang. | 1 1 1 | 2 2 6 |
| Echinochloa c.g. | 1 1 1 | 2 6 9 |
| Sorghum halepense | 1 1 1 | 4 7 9 |
| Rottboellia exaltata | 1 1 2 | 2 4 9 |

Compound A is 2-[4-(3,5-dichloropyridin-2-yloxy)-phenoxy]-propionic acid methyl ester, known from the German Offenlegungsschrift No. 2,546,251 and U.S. Patent Specification No. 3,046,553.

| | Compound | |
|---|---|---|
| Applied amount | 1 | B |
| kg/hectare | 2 1 ½ | 2 1 ½ |
| plant | | |
| soyabean | 9 9 9 | 9 9 9 |
| Avena fatua | 1 1 2 | 7 8 9 |
| Bromus tectorum | 1 1 1 | 4 6 9 |
| Lolium perenne | 1 1 1 | 1 2 4 |
| Alopecurus myos. | 1 1 1 | 1 2 3 |

Compound B is 2-[4-(5-chloropyridin-2-yloxy)-phenoxy]-propionic acid methyl ester, known from the German Offenlegungsschrift No. 2,546,251.

Post-emergence herbicidal action (contact herbicide)

A considerable number of weeds and cultivated plants, both monocotyledonous and dicotyledonous, are grown in pots in a greenhouse, and after emergence (in the 4- to 6-leaf stage) the plants are sprayed with an aqueous active-ingredient dispersion in varying dosages, expressed in kg of active ingredient per hectare, and the treated plants are kept at 24–26° C. with 45–60% relative humidity. The test results are evaluated two weeks after the treatment. The results are summarised below:

| | Compound | |
|---|---|---|
| Applied amount | 1 | A |
| kg/hectare | ½ ¼ ⅛ | ½ ¼ ⅛ |
| plant | | |
| wheat | 2 3 8 | 9 9 9 |
| soyabean | 8 8 9 | 9 9 9 |
| cotton | 6 7 8 | 9 9 9 |
| sugar beet | 7 8 8 | 9 9 9 |
| Avena fatua | 1 1 1 | 4 8 9 |
| Bromus tectorum | 4 6 7 | 9 9 9 |
| Alopecurus myos. | 1 2 2 | 3 5 8 |
| Digitaria sang. | 1 2 2 | 1 2 2 |
| Echinochloa c.g. | 1 1 1 | 1 1 2 |
| Sorghum halepense | 1 1 1 | 1 2 5 |

| | Compound | |
|---|---|---|
| Applied amount | 1 | B |
| kg/hectare | 2 1 ½ | 2 1 ½ |
| plant | | |
| soyabean | 9 9 9 | 9 9 9 |
| Avena fatua | 1 1 1 | 2 3 4 |
| Bromus tectorum | 2 2 4 | 6 7 8 |
| Lolium perenne | 1 1 1 | 3 5 6 |
| Alopecurus myos. | 1 1 1 | 3 4 5 |
| Digitaria sang. | 1 1 1 | 3 4 4 |

Compound B is 2-[4-(5-chloropyridin-2-yloxy)-phenoxy]-propionic acid methyl ester (see Offenlegungsschrift No. 2 No. 2,546,251).

Reduction of Growth of grasses

Seeds of the grasses Lolium perenne, Poa pratensis, Festuca ovina and Dactylis glomerata are sown in a soil/ peat/sand mixture (6:3:1) in plastic trays and watered in the usual manner. The emerged grasses are cut back each week to a height of 4 cm, and are sprayed 40 days after sowing and 1 day after the last cutting with an aqueous spray liquor of in each case a compound of the formula I. The amount of active ingredient is equivalent to 0.05–2 kg of active ingredient per hectare. The growth of the grasses is compared, 10 and 21 days after application, with that of the untreated control specimens. The compound of Example 1 when applied in an amount of 0.05 kg per hectare reduces the growth of the grasses by 18–32 %.

We claim:

1. A compound of the formula:

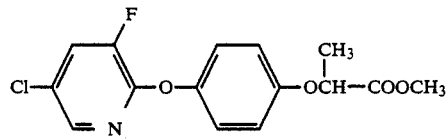

or the (R) (+) enantiomer thereof.

2. The (R)(+)-enantiomer of the compound of claim 1.

3. A herbicidal and plant-growth-regulating composition containing an effective amount of 2-[4-(5-Chloro-3-fluoropyridin-2-yloxy)-phenoxy]-propionic acid methyl ester according to claim 1, together with inert carrier material.

4. A herbicidal and plant-growth-regulating composition containing an effective amount of (R)(+) 2-[4-(5-Chloro-3-fluoropyridin-2-yloxy)-phenoxy]-propionic acid methyl ester according to claim 2, together with inert carrier material.

5. A method of selectively controlling weeds, which comprises applying thereto or to the locus thereof a herbicidally effective amount of 2-[4-(5-Chloro-3-fluoro-pyridin-2-yloxy)-phenoxy]-propionic acid methyl ester according to claim 1.

6. A method of selectively controlling weeds which comprises applying thereto or to the locus thereof a herbicidally effective amount (R)(+) 2-[4-(5-Chloro-3-fluoro-pyridin-2-yloxy)-phenoxy]-propionic acid methyl ester according to claim 2.

7. A method of reducing the growth of plants which comprises applying thereto or to the locus thereof an effective amount of 2-[4-(5-Chloro-3-fluoropyridin-2-yloxy)phenoxy]-propionic acid methyl ester according to claim 1.

8. A method of reducing the growth of plants which comprises applying thereto or to the locus thereof (R)(+)2-[4-(5-Chloro-3-fluoropyridin-2-yloxy)-phenoxy]-propionic acid methyl ester according to claim 1.

9. Methyl 2-[4-(5chloro-3-fluoro-2-pyridinyloxy)-phenoxy]propionate.

10. A compound of the formula:

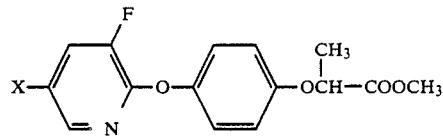

wherein X represents chloro or bromo, or the (R) (+) enantiomer thereof.

* * * * *